(12) United States Patent
Sunderland et al.

(10) Patent No.: US 11,541,234 B2
(45) Date of Patent: Jan. 3, 2023

(54) DETERMINING QUALITY OF ELECTRODE CONTACT WITH SKIN SURFACE

(71) Applicant: Mecta Corporation, Tualatin, OR (US)

(72) Inventors: Richard A. Sunderland, Des Moines, IA (US); John B. Shaw, Aloha, OR (US)

(*) Notice: Subject to any disclaimer, the term of this patent is extended or adjusted under 35 U.S.C. 154(b) by 0 days.

(21) Appl. No.: 17/207,483

(22) Filed: Mar. 19, 2021

(65) Prior Publication Data
US 2021/0290952 A1 Sep. 23, 2021

Related U.S. Application Data

(60) Provisional application No. 62/992,814, filed on Mar. 20, 2020.

(51) Int. Cl.
*A61N 1/36* (2006.01)
*A61N 1/08* (2006.01)
*A61N 1/04* (2006.01)

(52) U.S. Cl.
CPC ............ *A61N 1/08* (2013.01); *A61N 1/0488* (2013.01); *A61N 1/3603* (2017.08); *A61N 2001/083* (2013.01)

(58) Field of Classification Search
CPC ...... A61N 1/08; A61N 1/3603; A61N 1/0488; A61N 2001/083
See application file for complete search history.

(56) References Cited

U.S. PATENT DOCUMENTS

| | | | | |
|---|---|---|---|---|
| 6,014,587 A * | 1/2000 | Shaw | ...... | A61N 1/38 607/45 |
| 2014/0088394 A1* | 3/2014 | Sunderland | ...... | A61B 5/6843 600/373 |
| 2019/0343462 A1* | 11/2019 | Grant | ...... | A61B 5/7221 |

* cited by examiner

*Primary Examiner* — Ankit D Tejani
*Assistant Examiner* — Joshua Brendon Solomon
(74) *Attorney, Agent, or Firm* — Miller Nash LLP (57) ABSTRACT

A patient monitoring system within an Electroconvulsive Therapy (ECT) device includes a patient monitoring channel including a first electrode and a second electrode, with each electrode coupled to a respective lead. The monitoring system also includes an Alternating Current source structured to inject a test current to the first electrode lead or the second electrode lead and a differential amplifier structured to measure differences between signals received from the first electrode lead and the second electrode lead. Related methods include evaluating a quality of an electrode contact with a skin surface by injecting a lead of the electrode and one input of a differential amplifier with a known electrical current, comparing a difference between an electrical signal received from the lead of the injected electrode as well as from a lead of a passive signal electrode, and evaluating the compared difference.

15 Claims, 4 Drawing Sheets

DETERMINING QUALITY OF ELECTRODE CONTACT WITH SKIN SURFACE

CROSS-REFERENCE TO RELATED APPLICATIONS

This application is a non-provisional of and claims benefit from U.S. provisional patent application No. 62/992,814, titled SYSTEMS AND METHODS FOR DETERMINING QUALITY OF ELECTRODE CONTACT WITH SKIN SURFACE, filed Mar. 20, 2020, the disclosure of which is incorporated herein by reference in its entirety.

TECHNICAL FIELD

This disclosure is directed to the field of electro-convulsive therapy (ECT) and, more particularly, to determining a quality of electrode contact with the surface of a patient's skin.

BACKGROUND

A variety of electronic devices are designed to interact with a patient through electrodes that are applied to the patient's skin. Examples include electrocardiography (ECG), electroencephalography (EEG), and electromyography (EMG) devices. Such devices generally operate by making electrical contact with the patient's skin, through which contact electrical signals can pass.

The quality of the contact between an electrode and the patient's skin can greatly impact the quality of the signal obtained from the patient. Several factors can influence the quality of the connection. A significant factor is whether adequate skin preparation steps are taken before connecting the electrode to the patient's skin. A skin preparation process may include shaving the skin surface to remove hair, cleaning the skin surface, and lightly abrading the skin surface to remove dead skin cells. The electrode itself can also influence the quality of the connection. For example, electrolyte gel is often used in certain types of electrodes, and the gel can easily become dried out over time, losing its effectiveness.

Even in situations where an electrode appears to be well-connected to the patient's skin and skin preparation has been properly done, the quality of the electrical contact can still be relatively poor for certain patients. A visual or physical inspection of applied electrodes is generally inadequate for determining the quality of the connection. Also, a poor electrical connection can result in increased susceptibility to interference or complete inability of the device to provide usable signals from the patient.

Embodiments of the disclosed technology address these and other disadvantages of the conventional art.

DETAILED DESCRIPTION

Figure 1:
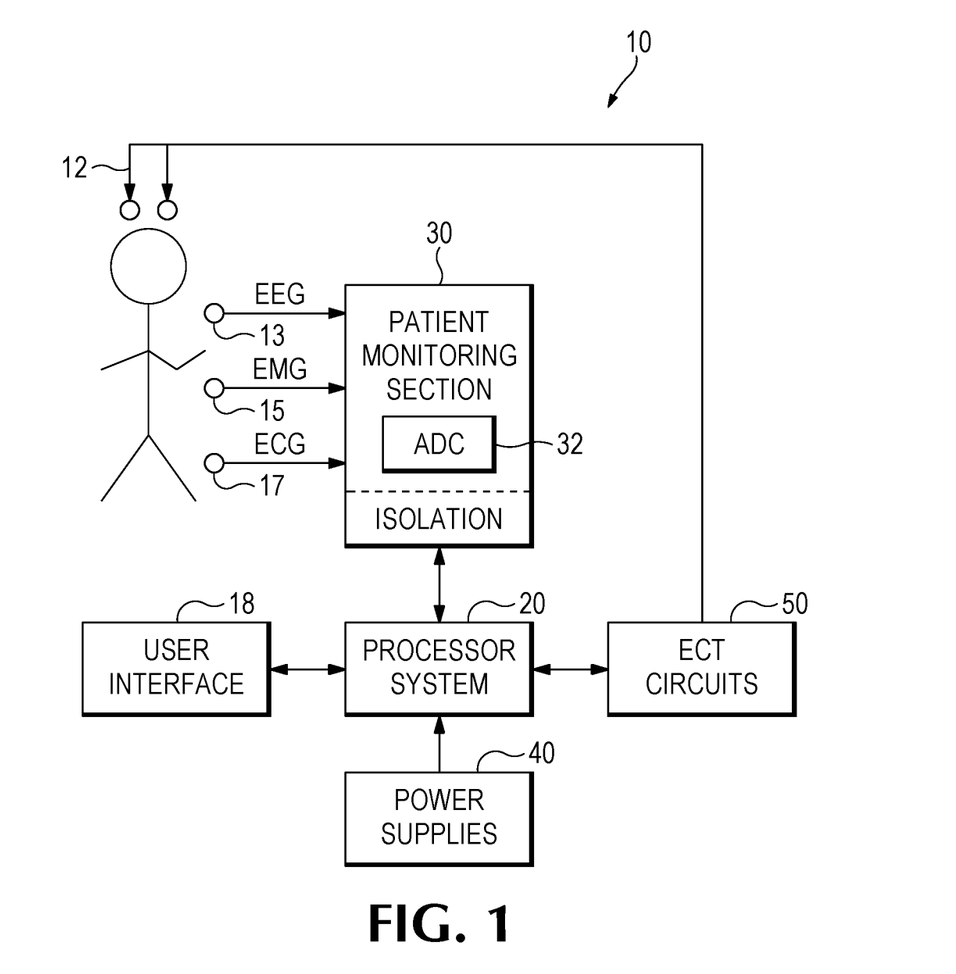
FIG. 1 is a functional block diagram of an ElectroConvulsive Therapy (ECT) system with patient monitoring according to embodiments of the disclosed technology.

FIG. 1 is a functional block diagram of an ElectroConvulsive Therapy (ECT) system 10 with patient monitoring in accordance with various embodiments of the disclosed technology.

Referring to FIG. 1, an ECT system 10 includes several connections to the patient. The first connection is the ECT stimulus electrodes 12 through which an ECT treatment signal is ultimately applied to the patient. The ECT system 10 also includes several patient monitoring signal electrode inputs 13, 15 and 17 that connect to the patient. Patient monitoring input 13 receives electroencephalography (EEG) signals from the patient. Patient monitoring input 15 receives electromyography (EMG) signals from the patient. Patient monitoring input 17 receives electrocardiography (ECG) signals from the patient. The monitoring inputs 13, 15, and 17 include signal electrodes that contact the skin of the patient. These electrodes receive electrical signals from the patient that can be used to monitor the patient. Embodiments of the disclosed technology ensure that the electrodes contact the patient's skin so that the signals may be received with adequate fidelity to maintain patient safety.

The overall system 10 further includes a user interface 18 through which the user, typically a psychiatrist or other medical doctor, interacts or interfaces with the ECT system 10. The user interface 18 may include a touch screen, for example. In other embodiments the user interface 18 may be a series of input switches and knobs. The user interface may further include a display screen by which the system 10 may display information to the user prior to, during, and following treatment. Such information may include traces of patient waveforms collected by the monitoring inputs 13, 15, 17. The user interface 18 may provide a menu of choices and controls for the user to configure which of the patient waveforms are displayed, as well as a gain factor or other quality of each waveform. The user interface 18 may also include a chart recorder to provide a hard copy output of the patient monitoring signals.

A processor system 20 orchestrates the operation of the system. The processor 20 may include a number of independent processors or processor functions, such as a system processor, a safety processor, a digital signal processor, and a user interface processor. Of course in some embodiments more, fewer, or different processors may be used. In general, these processors in the system processor 20 control the operation of the ECT system 10, including interacting with the user, generating the therapeutic ECT signal, monitoring the patient, ensuring patient safety, and creating a record of the treatment session, among other functions.

The system processor 20 is also coupled to a patient monitoring section 30 to configure the patient monitoring section 30 into various modes responsive thereto. These modes include a normal operational mode in which the patient monitoring signals are received from the patient, an electrode contact impedance mode, and one or more test modes wherein the accuracy of the patient monitoring section 30 is tested. The patient monitoring section 30 includes an Analog to Digital Converter (ADC) 32 to digitize the patient monitoring signals received at inputs 13, 15 and 17 (i.e., the EEG, EMG and ECG signals). This digitized data is then operated on by portions of the processor system 20 to extract electrode contact impedance information, as well as to filter out unwanted power line frequency interference and other interference. The filtering may be performed by finite impulse response (FIR) filters, or infinite impulse response (IIR) filters, for example.

One or more power supplies 40 provide power to operate the system 10 as well as to generate the ECT Therapy signal. The ECT Therapy signal is generated and managed, in the illustrated embodiment, by an ECT circuit block 50. In certain cases, delivering ECT pulses through separate treatment electrodes 12 to the scalp of an anesthetized psychiatric patient is intended to trigger a seizure, which seizures are generally therapeutic in treating certain psychiatric disorders.

The construction and operation of an example ECT system 10 is described in greater detail in U.S. Pat. Nos. 5,755,744 and 6,014,587, which are herein incorporated by reference in their entirety.

As described above, the patient monitoring section 30 may acquire EEG signals from that patient's scalp and EMG signals from a patient's limb. The monitoring section 30 may also acquire an ECG signal from the patient. After an ECT treatment is delivered to the patient from the ECT circuit block 50, the patient's EEG and EMG signals received from the patient monitoring section 30 may be analyzed to determine if the triggered seizure was sufficient for therapeutic purposes. Furthermore, the patient's ECG signals are indicative of whether the ECT treatment has caused any cardiac rhythm problems. In situations where the electrical contact impedance of a patient's EEG and/or EMG electrodes becomes too high, waveforms acquired through such electrodes become much noisier and filled with artifacts, possibly to a point at which the worsened signal quality makes the EEG and/or EMG waveforms useless for analysis of seizure efficacy. Systems and devices in accordance with the disclosed technology may include internal hardware which supports being able to measure and report the contact impedance of each individual signal electrode so that the clinician can replace or re-apply problematic electrodes before delivering an ECT treatment.

Many existing ECT, EEG, and EMG devices do not contain a built-in capability to evaluate signal electrode contact quality. Users wishing to obtain this information are consequently forced to use separate, stand-alone electrode contact quality-measuring devices. This is generally a significant concern, and it is much more convenient to have such measurement capability integrated within the ECT, EEG or EMG devices themselves. Embodiments of the invention are directed to a device that includes an ability to evaluate a quality of electrical contact between a patient and signal electrodes attached to the patient.

Certain embodiments of the disclosed technology include ECT systems and methods that are configured to evaluate the quality of the connections made between body surface electrodes and a patient's skin. It is advantageous to maximize this quality because the quality of those electrode connections affects the quality of electrical signals that may be obtained through them. An electrode contact quality evaluation circuit may be configured to perform the quality evaluation by determining the contact impedances of the electrodes. The corresponding contact quality of each electrode may be conveyed to the user.

A device in accordance with the disclosed technology may include multiple EEG channels, an EMG channel, and an ECG channel—each of which have their own two signal electrodes, and all of which have their output signal quality affected by the contact quality of their respective body surface electrodes.

Figure 2:
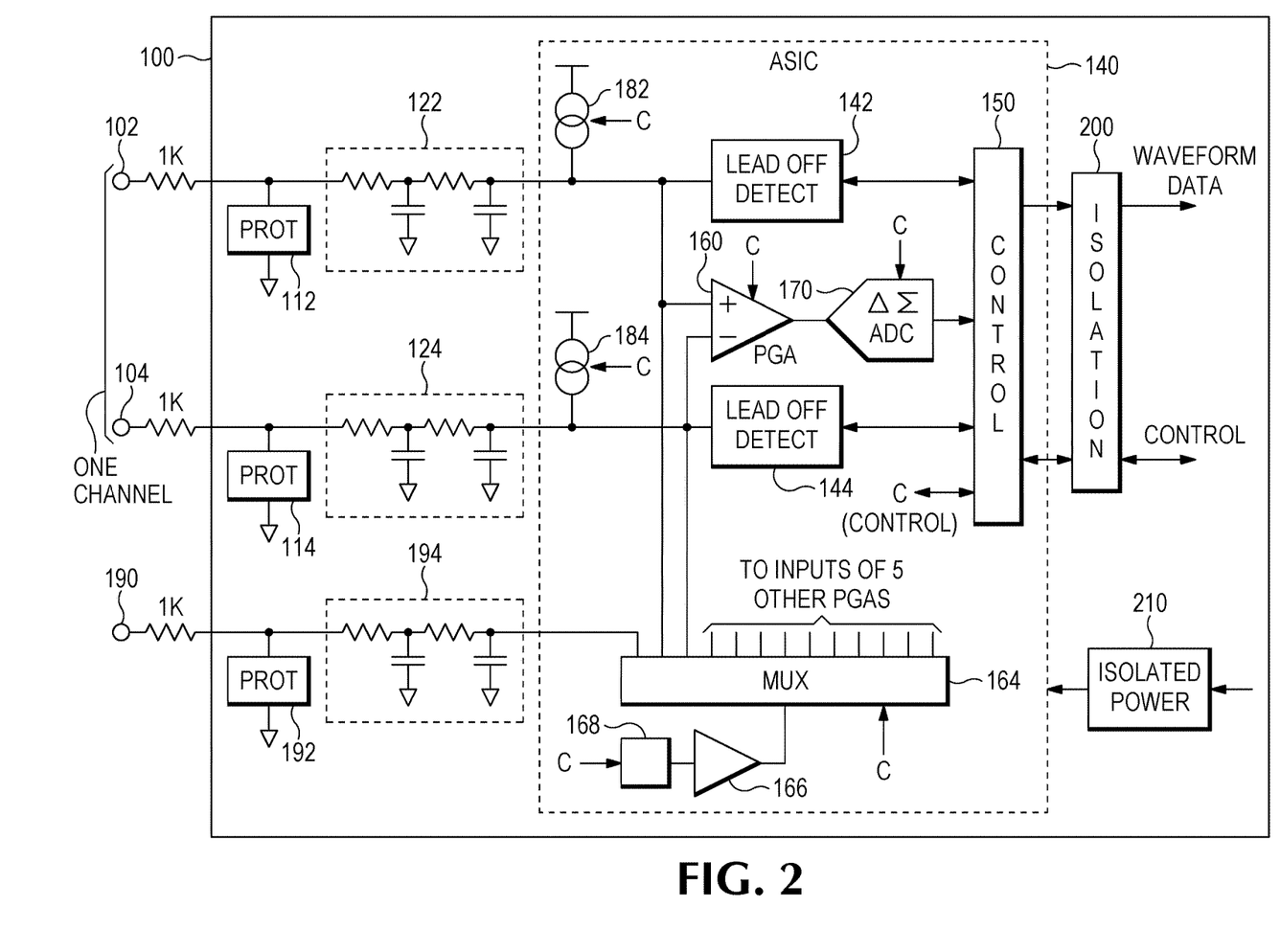
FIG. 2 is a schematic block diagram of example components of the patient monitoring portion of FIG. 1, according to embodiments of the disclosure

FIG. 2 is a block diagram of example components of the patient monitoring subsystem 100, according to embodiments of the disclosure. The patient monitoring subsystem 100 may be an example implementation of the patient monitoring portion 30 illustrated in FIG. 1. Other embodiments, of course, may include different devices capable of performing the same or similar functions to those described with respect to patient monitoring portion 100.

The patient monitoring subsystem 100 of FIG. 2 includes a pair of patient signal electrodes 102, 104, which make up a single channel. Certain patient monitoring subsystems may include one or more channels. For example, EMG and ECG patient monitoring channels typically use only one channel each in an ECT device, each channel utilizing inputs from a pair of electrodes. An EEG patient monitoring channel may use four channels, for example, again, with each channel utilizing inputs from a pair of electrodes, such as the electrode pair 102, 104.

Electrode 102, is coupled to a protection circuit 112, while electrode 104 is coupled to a protection circuit 114. These protection circuits 112, 114 protect the patient monitoring subsystem 100, and, by extension, the system 10 from electrical currents that could damage the patient monitoring subsystem 100. The protection circuits 112, 114 provide protection from ECT therapy pulses and Electro-Static Discharge (ESD), for example, as well as from any defibrillator discharges near the ECG electrodes and from other potentially damaging stray voltages and currents.

Each of the electrodes is also coupled to a respective low pass filter. Electrode 102 is coupled to a low pass filter 122, while electrode 104 is coupled to a low pass filter 124. In the illustrated embodiment the low pass filters 122, 124, are constructed from resistors and capacitors, which may vary in resistance and capacitance values. In other embodiments the low pass filters 122, 124 may be formed of other components, or in other configurations. In one embodiment the low pass filters 122, 124 are structured to pass signals from Direct Current (DC) through approximately tens of kHz before signal processing, while in other embodiments the low pass filters are structured to pass signals up to approximately 6 kHz before signal processing. The degree of filtering and the filtered frequencies may be implementation specific.

The resistors, and to a very slight extent, the capacitors, in the low pass filters 122, 124 contribute to a total impedance of an electrode path. In one embodiment the low pass filters 122, 124 add approximately 50 kOhms. Further, the electrical connection to each electrode may include a 1 kOhm series resistor. In designs that utilize patient trunk cables, the cables themselves may contain the series resistors. In designs that use only lead wires, the series resistors may be included within the monitoring subsystem 100 on the patient side of the protection circuits, or may be located at the junction between the lead wire and the actual electrode.

Some embodiments of the patient monitoring subsystem 100 may include an Application Specific Integrated Circuit (ASIC), which integrates many circuits within it. FIG. 2 illustrates an ASIC 140, which includes circuits used to perform many of the functions described herein. Of course, such circuits may be made from discrete devices and retain the same functionality as that described herein occurring within the ASIC 140. One benefit to including an ASIC 140 in the design of the patient monitoring subsystem 100 is that the ASIC is programmable. A control system 150 within the ASIC 140 may be so programmed to control the functions of the ASIC and the circuitry within it as described below.

The ASIC 140 includes lead-off detection circuitry. The electrode 102 is coupled to a lead-off detection circuit 142, while the electrode 104 is coupled to a lead-off detection circuit 144. The lead-off detection circuits 142, 144 determine whether its electrode is electrically connected to a patient or not. If an electrode has separated from the patient, its lead-off detection circuit will notify the appropriate processor in the system 10, to, in turn, notify the user that the lead has separated from the patient.

Each pair of signal electrodes 102, 104 is coupled to a differential instrumentation amplifier, such as a Programmable Gain Amplifier (PGA) 160. The PGA 160 includes two inputs, each coupled to one of the electrodes 102, 104, for measuring voltage differences between the electrodes and amplifying the voltage difference. The amount of amplification in the PGA 160 is controllable, and specifically controllable through the control system 150. The output of the PGA 160 is coupled to an Analog to Digital Converter (ADC) 170, which may be of the delta-sigma type. The ADC 170 converts the analog output signal from the PGA 160 to a digital signal for use by the system 10.

In embodiments of the invention, each electrode is coupled to a current source for injecting a signal into the electrode for test purposes. These current sources are each programmable with respect to frequency, phase, and amplitude (including off). In the illustrated embodiment of FIG. 2, the electrode 102 is coupled to a current source 182 and the electrode 104 is coupled to a current source 184. The operation of the respective current sources 182, 184 is described below.

In the illustrated embodiment, each of the elements described above, including the electrodes 102, 104, protection circuits 112, 114, low pass filters 122, 124, lead-off detectors 142, 144, the PGA 160, the ADC 170, and the current sources 182, 184 collectively make up one signal channel of the patient monitoring subsystem 100. As described above, various types of patient monitoring use different numbers of channels. Although only a single channel is illustrated in the patient monitoring subsystem 100 of FIG. 2, embodiments of the invention include the components to make up the number of channels desired. In one embodiment the patient monitoring subsystem 100 includes six channels, while in other patient monitoring subsystems may include more or fewer channels.

In addition to the channel hardware, described above, the patient monitoring subsystem 100 includes a reference electrode 190, its protection circuit 192, and its low pass filter 194. These components operate the same or similarly to their equivalents described above with reference to signal electrodes 102 and 104, and therefore description of their functions is omitted for brevity.

An analog multiplexer 164 is coupled to each of the separate signal channels, and may be used to select one of the channels for operations as described below. Further, the ASIC 140 includes an amplifier 166 that is used to drive the reference electrode 190 to improve the patient monitoring system's common mode rejection during normal operation, or is used to hold a selected signal electrode at a fixed voltage while evaluating the contact impedance of a different signal electrode. Reference driver source selector 168 selects the input source for the amplifier 166. The input for the amplifier 166 comes from either the common mode content of selected signal channels during normal operation, or comes from a mid-supply fixed voltage while determining contact quality of electrodes.

As illustrated in FIG. 2, many of the components listed above may be controlled by the programmable control system 150. Such controllable components include the PGA 160, ADC 170, current sources 182, 184, multiplexer 164 and reference driver source selector 168.

The ASIC 140 is coupled to isolation circuitry 200, which electrically isolates the digitized patient signals generated by the patient monitoring subsystem 100 and the digital status and control signals between the patient monitoring subsystem 100 and the processor system 20 from earth ground, and from the electrical power elsewhere in the system 10. A power supply 210 is also isolated from the main power used elsewhere in the system 10, and supplies isolated power to the ASIC 140, for use by the system, as described below.

Returning back to description of the disclosed technology, clinical experience indicates that impedances of the electrical contact between an electrode and the patient's skin measured at approximately 30 Hz are satisfactory if they are less than 5 kOhms. Devices in accordance with the disclosed technology should therefore use a test frequency of approximately 30 Hz to test for the quality of contact between an electrode and the patient's skin. In some embodiments the frequency may be preferably between 30-35 Hz, and more preferably 32 Hz.

Electrode contact impedance as described herein has a real component and a reactive component. Both components are non-linear, and both components vary approximately inversely with the measurement current's frequency. Direct Current (DC) measurements are highly subject to DC electrode offsets, so they are generally not reliable for indicating an electrode's skin contact quality. As such, Alternating Current (AC) impedance measurements are preferably used. A sine wave shape may be used for this testing, but it is usually simpler to use a square wave shape. Embodiments of the invention may use either a sine wave, a square wave, or waves having other, repeated shapes.

As described above, each electrode path includes a resistance of approximately 50 kOhms in its low pass filter, for instance low pass filter 122, and an additional 1 kOhm resistance near the electrode itself. Because the frequency of the test current is relatively low, the effects on impedance of the small capacitances in these input low pass filters and patient cable may be neglected. Indeed, performing a current injection at the signal's amplifier input takes advantage of the passive filtering that occurs between the injection point and the patient electrode, to provide protection of the amplifier and current injection circuitry from damage that otherwise might occur during ECT pulses or, in other embodiments, while defibrillating the patient. The techniques described herein inherently include these passive resistances in all measurements of electrode contact impedances. Hence, to obtain the actual electrode contact impedance, this component, e.g., 51 kOhms, is subtracted from the measured total. In some embodiments the system processor is programmed to perform this operation.

In some embodiments, electrode contact impedance testing may occur while EEG, EMG, and ECG signals are still being received from a patient. In other embodiments the testing may occur when such signals are not being received. In those situations where electrode testing occurs while signals are being received from the patient, to minimize the impact on accuracy, the amplitude of an AC test current used during electrode impedance testing may be made as large as possible, subject to patient safe current limitations, to obtain a suitably-high test-signal-to-patient signal ratio. This advantageously ensures that the contact quality test signals will be orders of magnitude larger in amplitude than the patient's physiological signal contributions. Because the signals created by the test currents are so much larger than the patient's physiological signals, it is convenient to use a programmable gain amplifier (PGA) rather than a fixed gain amplifier. This programmability advantageously allows the amplifier gain to be reduced during electrode contact impedance testing below the gain used during normal operation, thereby preventing amplifier saturation.

In certain embodiments, electrode contact quality will be measured only for those electrodes that previously have been detected by other means as being connected to the patient. In other words, a contact quality is not measured or evaluated on electrodes that are not presently connected to a patient. Electrode connection status of each electrode may be checked using conventional techniques, for example, by using DC test currents or other methods.

As described above, a reference electrode is additionally connected to the patient during all operating modes. Notably, poor contact quality of the reference electrode does not typically affect the quality of the signals that are obtained from the patient as much as does poor contact quality of the signal electrodes.

The description below generally applies to patient signal electrodes. As described above, a typical channel includes two signal electrodes, such as the electrodes 102 and 104 that are used by a single channel. In this disclosure, one of the signal electrodes is referred to as the positive (+) electrode of the channel while the other electrode of the channel is referred to as the negative (−) electrode. Although the following description is described as measuring the contact impedance of a channel x's positive (+) signal electrode (where "x" indicates a particular one of the device's multiple channels to be injected with the test current), the process for measuring the contact impedance of channel x's negative (−) signal electrode differs only by enabling the test current for channel x's − electrode and disabling channel x's test current for the + electrode. The impedances that are internal to the patient may typically be ignored in this analysis because they are significantly smaller than the electrode contact impedances and the resistance of the channel's passive low pass input filters.

Figure 3:
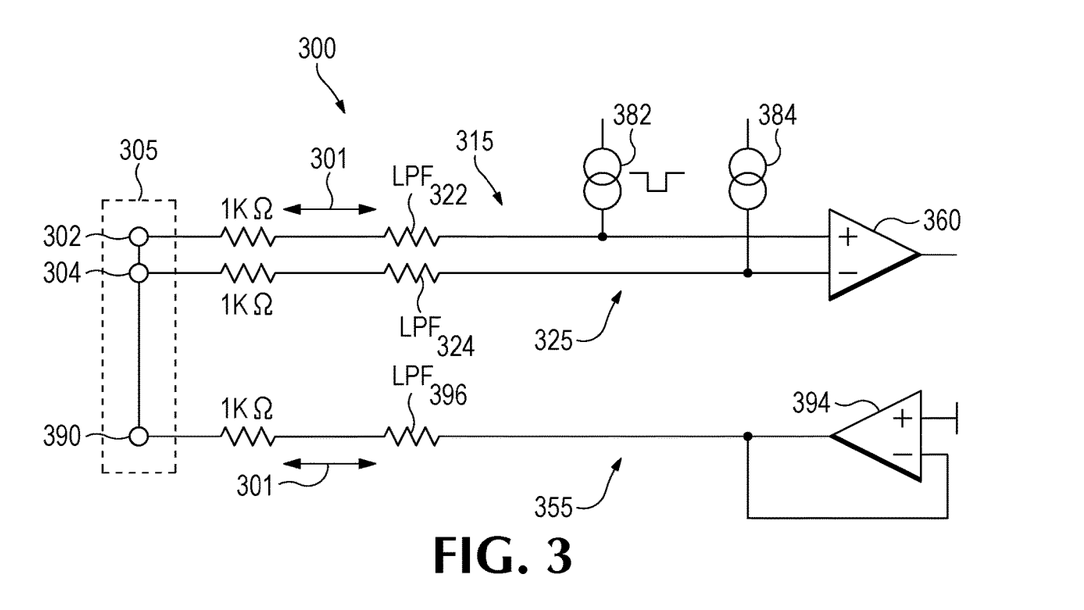
FIG. 3 is a functional block diagram of a single electrode contact impedance measurement system 300 configured to evaluate a connection between a single electrode and a patient's skin surface according to embodiments of the disclosure.

FIG. 3 is a functional block diagram of a single electrode contact impedance measurement system 300 configured to evaluate a connection between a single electrode and a patient's skin surface according to embodiments of the disclosure. The system 300 includes two monitoring (signal) electrodes that are applied to the skin of a patient 305: a first electrode 302 used for injection, a second electrode 304 used for sensing, and another electrode 390, also referred to herein as a return electrode.

The system 300 also includes an injection electrode selection circuit 315 that is configured to supply a test current to the selected injection electrode 302, and a sense electrode selection circuit 325 that is configured to supply a signal obtained from the sense electrode 304. The system 300 also includes a non-driven return circuit 355, through which the test current may be returned to/from the return electrode 390.

The system 300 also includes an AC current source 382 that is configured to generate a test current 301, and differential measurement circuitry 360 that is configured to measure the difference between the signals present at the + input of the amplifier 360 and the sense electrode 304. In some embodiments the measurement circuitry amplifier 360 is a programmable Gain Amplifier, such as the PGA 160 described above with reference to FIG. 2. An AC current source 384 is configured to be off while testing electrode 302, but is turned on while testing electrode 304, in which latter case the current source 382 would be off.

The system 300 further includes a processing device (not shown in FIG. 3) that is configured to evaluate the difference sensed by the measurement circuitry 360 and generate an output representing a quality of the first electrode's contact with the patient's skin surface. Such an output may be presented on the user interface 18 of the system 10 to inform the user of the device about the quality of the connection between the patient monitoring signal electrodes and the patient.

In this example, a 32 Hz square wave of current is injected by the current source 382 into the + input of the PGA 360 in the patient monitoring channels. The current then passes out through that input's passive low pass filter 322 to the + signal electrode 302 itself, through the + signal electrode's contact impedance, and into the patient. During this testing period, the current source 384 for that PGA's − input is disabled (i.e., there is zero lead-off detection current through the latter's input filter and the signal electrode's contact impedance). Hence, there is zero square wave voltage drop across the latter two impedances, so that the voltage at the PGA 360's − input equals the voltage at the sensed electrode 304.

All of the lead-off detection current passes through the return electrode 390's contact impedance and the impedance of its low pass filter 396, and is sunk by a fixed voltage source 394 that keeps the PGA 360 inputs within their dynamic range. The common mode rejection of the PGA 360 allows its output to respond only to the voltage differential between its two inputs. Because of this action, the peak-to-peak output of the PGA 360 is equal to the product of the peak-to-peak test current 301 multiplied by the sum of the impedance of the low pass filter 322+1 kOhm and the contact impedance of the + signal electrode 302.

Since the impedance of the low pass filter 322 is fixed and known, the voltage drop across the low pass filter 322+1 kOhm, multiplied by the gain of the PGA 360, may be subtracted from the total output of the PGA 360, leaving just the voltage drop across the contact impedance of the + signal electrode 302, which is what was desired to be tested. The test as described above tests exactly the quality of the contact between the patient's skin and the + electrode 302. Further, because the test current from the current source 382 is a true current source, the voltage drop across the contact impedance of the + electrode 302 is independent of the voltage drop across the contact impedance of the return electrode 390. Comparators within the lead-off detectors 142 and 144 that are typically used to detect lead off conditions within each channel may be used to determine if the injected input is being pulled too close to a PGA 360's supply rail. However, even under such conditions, the output of the PGA 360 will still exceed a voltage that indicates an unacceptably high signal electrode impedance.

Testing the contact impedance of the negative (−) electrode 304 occurs in the same manner, except that current is injected to the − input of the PGA 360 through the current source 384, while the current source 382 is turned off. Because the PGA 360 measures a voltage differential between its inputs, it does not matter which of the current sources 382 or 384 are injecting current, and the PGA 360 measures the voltage differential in the same way for either case.

In the example, a gain of 1× may be used for the gain of the PGA 360. This gain is generally low enough so that the inputs to the PGA 360 may stay within their acceptable common mode input range and the output of the PGA 360 will not saturate even with relatively large electrode contact impedances and with the maximum expected +/−300 mV of DC electrode offset.

Figure 4:
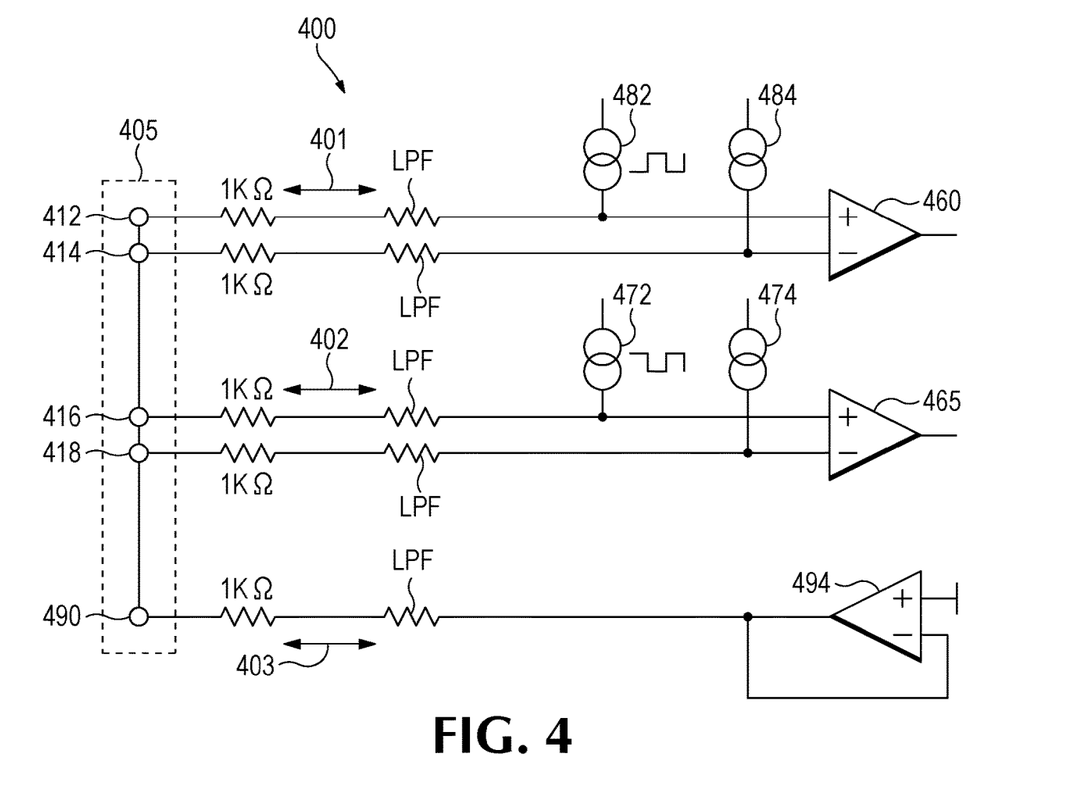
FIG. 4 is a block diagram of an electrode contact impedance measurement system 400 for two electrodes, configured to evaluate a connection between multiple electrodes and a patient's skin surface in accordance with certain implementations of the disclosed technology.

FIG. 4 is a block diagram of an electrode contact impedance measurement system 400 for two electrodes, configured to evaluate a connection between multiple electrodes and a patient's skin surface in accordance with certain implementations of the disclosed technology. The system 400 is similar to the system 300 illustrated by FIG. 3 but, in this example, there are two pairs of signal electrodes, including a first injected electrode 412 with its sensed electrode 414, and a second injected electrode 416 with its sensed electrode 418. Electrodes 412 and 416 are injected with test signals 401 and 402, respectively, from AC current sources 482 and 472, respectively. Current sources 484 and 474 are both configured to be off while testing the (+) positive electrodes 412 and 416, but would be on while testing the (−) negative electrodes 414 and 418. Separate amplifiers 460 and 465 handle the contact impedance signals from each pair of injected and sensed electrodes. The system 400 also includes a single return electrode 490 that serves as the return path for the algebraic sum 403 of both test currents 401 and 402. Alternatively, the sense function may be provided from just electrode 414 or from just 418 to the − inputs of both the amplifiers 460 and 465 simultaneously, if desired. The amplifiers 460 and 465 may be Programmable Gain Amplifiers, such as the PGA 160 described with reference to FIG. 2.

Because it may take significant time to perform separate contact quality measurements for each of the electrodes, and because patient monitoring is typically disrupted during the entire electrode contact measurement process, it minimizes test time to simultaneously measure the contact quality of multiple electrodes. If the contact quality of multiple signal electrodes are to be measured simultaneously, it is advantageous to minimize the total current that passes through the sum of the reference electrode 490's contact impedance and the input filter resistance (194 in FIG. 2) used for the reference electrode. This minimization of current facilitates maintaining linear PGA operation despite the use of multiple test currents, even with a higher contact impedance in the reference electrode. The net current through the reference electrode may be minimized by using opposing phases of test currents while multiple electrodes are injected simultaneously. This approach for simultaneous measurements of the contact quality of multiple electrodes can easily be modified for different combinations of signal electrodes.

Figure 5:
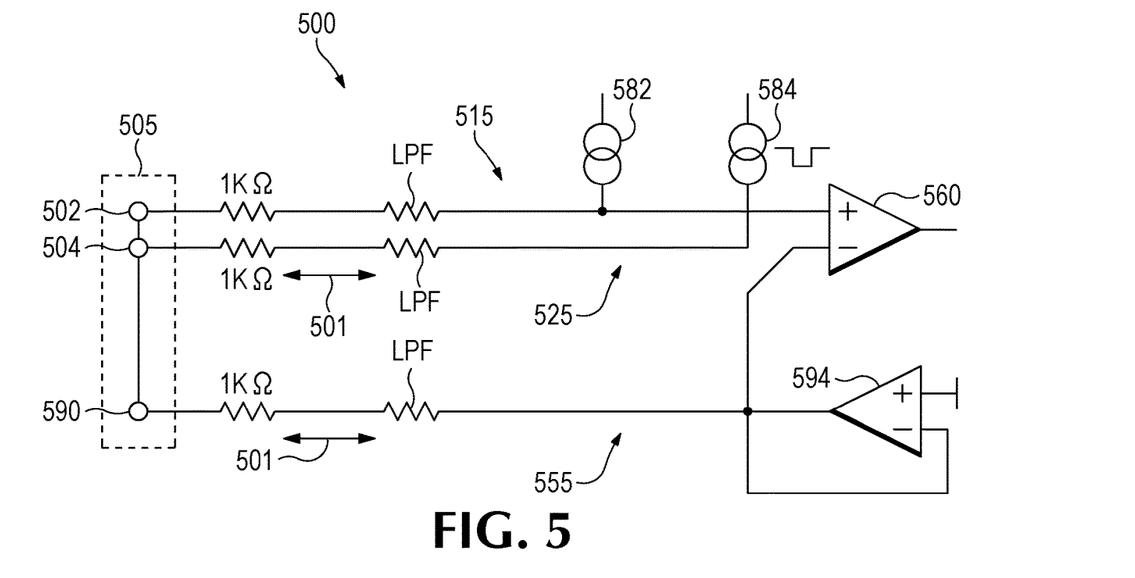
FIG. 5 is a block diagram of a reference electrode contact impedance measurement system 500 configured to evaluate a connection between a reference electrode 590 and a patient's skin surface in accordance with certain implementations of the disclosed technology.

FIG. 5 is a block diagram of a reference electrode contact impedance measurement system 500 configured to evaluate a connection between a reference electrode 590 and a patient's skin surface in accordance with certain implementations of the disclosed technology.

Measuring the contact impedance of the reference electrode 590 involves injecting a test current 501 from a current source 584 through a single injection electrode 504 that is not otherwise used in this particular measurement while measuring the voltage difference between the patient (at the electrode 502) and the output 555 of the reference electrode driver 594. In this example, the current source 582 is configured to be off, so there is no current flowing through either the contact impedance of the sensed electrode 502 or the impedance of the low pass filter coupled thereto, so that the voltage at the + input of the PGA 560 is equal to the sensed voltage on the patient. The output of the PGA 560 includes a component that is caused by the test current 501 flowing through the low pass filter of the reference path+1 kOhm, and that is typically subtracted from the total.

A single electrode of any connected channel can be injected with its test current, and that channel's PGA can be used for measuring the contact impedance of the reference electrode after the reference electrode and that channel are fully connected.

Since higher contact impedance is generally more tolerable in the REF electrode than in signal electrodes, an acceptable alternative to actually measuring the contact impedance of the reference electrode is simply to determine if the test current is pulling the voltage at the injected input of the PGA too close to either acceptable common mode input voltage limit of the PGA. Comparators within the lead-off detectors 142, 144 (FIG. 2) that are normally used only to detect lead-off conditions at each electrode input can be used to determine if the injected input is being pulled too close to a PGA supply rail.

During electrode contact quality testing, the peak-to-peak voltage at the output of a channel's PGA (as digitized by that channel's ADC) is equal to the PGA gain times the peak-to-peak test current multiplied by the sum of the contact impedance of the electrode that is being injected, plus the approximate (50 kOhm) resistance of that electrode's low pass filter and the 1 kOhm resistance that is typically inserted into patient cables. If the magnitude of the AC test current is not known exactly, it will be important to determine its actual magnitude before the electrode contact impedances can be correctly calculated. Depending on the exact design used, the magnitudes of test currents may be different for different channels, so a calibration factor is preferably performed for each channel. Because the peak-to-peak PGA outputs are what is needed for accurate measurement of the contact impedance, only the peak-to-peak calibration is needed for each test current. That is, it is not necessary to obtain separate calibration factors for the components of pull-up currents and pull-down currents.

If the test current magnitudes do not vary with device temperature or vary over the product lifetime, the calibration factors may be obtained while all electrode inputs, including the REF electrode input, are shorted together, and just one AC test current may be applied at a time. Since the resistances of the input filters are all known and stable with time and temperature, the peak-to-peak PGA output voltages thus obtained can be divided by the known input filter resistances to obtain the test current calibration factor for each test current, i.e., one at a time. The device 10 may store these calibration factors in a non-volatile memory, for use over the lifetime of the device.

If instead the calibration factors of a design's test currents can vary significantly with time or with changes in that device's internal temperature over the device's lifetime, then a method may be employed that can update these calibration factors periodically or as needed. One possible method for including such provisions internally is to include a structure or method for connecting one channel's PGA input at a time to a fixed internal resistor (e.g. 50 kOhms) at such time as the inputs to that PGA are not connected to a patient. The calibration factor for that channel's test currents may be calculated from that channel's PGA's output, since the unknown test current is then passing only through a known resistance.

After its calibration factor is obtained, any single channel's lead off detection current can be used for measuring the contact impedance of the reference electrode after the reference electrode and that channel are fully connected.

An electrode contact quality evaluation device in accordance with certain implementations of the disclosed technology may be configured to evaluate a connection between an electrode and a skin surface.

The electrode contact quality evaluation device may include an AC current source configured to generate a test current, an injection electrode selection circuit configured to supply a test current to at least one selected injection electrode through at least one selected injection lead, a non-driven return circuit through which the test current or the algebraic sum of multiple test currents may be returned, and a sense electrode selection circuit configured to supply at least one signal obtained from at least one selected sense electrode through at least one selected sense lead.

The device may also include differential measurement circuitry configured to measure the difference between the signals present on at at least one injection electrode and on at least one sensed electrode, and a processing device configured to evaluate the difference(s) and generate outputs representing a quality of at least one connection between at least one of the electrodes and the skin surface.

In certain embodiments, the non-driven return circuit of the electrode contact quality evaluation device may provide a passive path to a fixed supply as the return path for the test current or the algebraic sum of multiple test currents.

In certain embodiments, the differential measurement circuitry electrode contact quality evaluation device may include one or more differential amplifiers coupled to the inboard end of the input filter of one or more selected injection electrodes and to the inboard end of the input filter of one or more selected sense electrodes.

In certain embodiments, the output(s) of the one or more differential amplifiers may be converted from analog signals to digital signals by one or more analog to digital convertors. These digital signal(s) may be provided to the processing system.

In certain embodiments, the non-driven return circuit of the electrode contact quality evaluation device may include at least a buffer amplifier configured to buffer a fixed voltage to keep the inputs of the differential amplifier(s) within their input common mode specifications.

In certain embodiments of the electrode contact quality evaluation device, the current source is a square wave generator.

In certain embodiments, the magnitude of current through the return electrode may be minimized by using opposing phases of test currents while multiple electrodes are injected simultaneously with test currents.

A method of evaluating the quality of electrode contact with a skin surface in accordance with certain implementations of the disclosed technology, used for patient monitoring channels (e.g., EEG, ECG, and/or EMG) included in an ECT device, may include checking for and determining that at least three electrodes are in physical contact with a skin surface using electrode contact detection circuitry, and evaluating and determining a quality of an electrical connection between at least one of the electrodes and the skin surface using electrode contact quality evaluation circuitry.

In certain embodiments, the evaluating and determining may include selecting at least one of the electrodes as an injection electrode, at least another electrode as a sense electrode, and another of the electrodes as a return electrode, applying a test signal or test signals to the injection electrode or electrodes, allowing the non-driven return electrode to serve as the return path for the sum of one or more test signals, and computing at least one contact impedance for one of the injection electrodes. The method may further include inhibiting ECT operations if the quality of the electrode contact is below a certain threshold, for example.

Aspects of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, FPGA, and the like. Particular data structures may be used to more effectively implement one or more aspects of the disclosure, and such data structures are contemplated within the scope of computer executable instructions and computer-usable data described herein.

The disclosed aspects may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

All features disclosed in the specification, including the claims, abstract, and drawings, and all steps or operations in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

We claim:

1. A patient monitoring system within an Electroconvulsive Therapy (ECT) device, the patient monitoring system comprising:
   a patient monitoring channel including a first electrode and a second electrode, each electrode coupled to a respective lead;
   a first lead off detection circuit coupled to the first electrode lead;
   a second lead off detection circuit coupled to the second electrode lead;

an Alternating Current source structured to inject a test current to the first electrode lead or the second electrode lead;

a return electrode coupled to the first lead off detection circuit and the second lead off detection circuit;

a differential amplifier structured to measure differences between signals received from the first electrode lead and the second electrode lead to detect a quality of an electrical contact of the respective electrode; and a current sinking circuit coupled to the return electrode and configured to sink current sourced from either the first lead off detection circuit or the second lead off detection circuit, the current sinking circuit structured to dynamically maintain the differential amplifier within an operating range.

2. The patient monitoring system according to claim 1, further comprising a threshold comparator to compare the output of the differential amplifier to a predetermined threshold.

3. A method of evaluating a quality of an electrode contact with a skin surface, the method comprising:

injecting a lead of the electrode and one input of a differential amplifier with a known electrical current from an impedance measuring circuit;

injecting the lead of the electrode with a current from a lead off detecting circuit;

sinking the current from the lead detecting circuit with a current sinking circuit coupled to a reference electrode to maintain the differential amplifier in an operation mode;

comparing a difference between an electrical signal received from the lead of the injected electrode as well as from a lead of a passive sensed electrode; and evaluating the compared difference.

4. The method of evaluating a quality of an electrode contact according to claim 3, in which evaluating the compared difference comprises comparing the compared difference to a predetermined threshold.

5. The method of evaluating a quality of an electrode contact according to claim 3, in which the electrode is an electrode in an EEG channel, an ECG channel, or an EMG channel.

6. The patient monitoring system according to claim 1, in which the Alternating Current source is structured to inject a test current into the first electrode lead, and further comprising a second Alternating Current Source structured to inject a second test current into the second electrode lead.

7. The patient monitoring system according to claim 1, further comprising:

a second patient monitoring channel including a third electrode and a fourth electrode, each electrode coupled to a respective lead;

a second Alternating Current source structured to inject a second test current to the third electrode lead or the fourth electrode lead, the second test current having an opposite phase of the test current from the Alternating Current source.

8. The patient monitoring system according to claim 7, further comprising:

a second differential amplifier structured to measure differences between signals received from the third electrode lead and the fourth electrode lead.

9. The patient monitoring system according to claim 8, further comprising:

a third lead off detection circuit coupled to the third electrode; and a fourth lead off detection circuit coupled to the fourth electrode;

in which the return electrode is further coupled to the third lead off detection circuit and the fourth lead off detection circuit.

10. The patient monitoring system according to claim 9, in which the a current sinking circuit coupled to the return electrode is configured to sink current sourced from either the third lead off detection circuit or the fourth lead off detection circuit, and in which the current sinking circuit is structured to dynamically maintain the second differential amplifier within an operating range.

11. The patient monitoring system according to claim 1, further comprising a low pass filter coupled between the Alternating Current Source and the first electrode.

12. The patient monitoring system according to claim 11, in which the effect of the passing the test current through the low pass filter is subtracted from an output of the differential amplifier.

13. The patient monitoring system according to claim 1, in which the Alternating Current source is structured to inject a test current into the first electrode lead, and further comprising a second Alternating Current Source structured to inject a second test current into the second electrode lead.

14. The method according to claim 3, further comprising:

injecting a lead of a second electrode and a second input of the differential amplifier with a second known electrical current from a second impedance measuring circuit;

injecting the lead of the second electrode with a current from a second lead off detecting circuit; and sinking the current from the second lead off detecting circuit.

15. The method according to claim 14, further comprising:

determining a quality measurement of the electrode and the second electrode from the compared difference evaluation.

* * * * *